United States Patent [19]

Burello et al.

[11] Patent Number: 5,364,968
[45] Date of Patent: Nov. 15, 1994

[54] HERBICIDE INTERMEDIATE O-NITROPHENYL CYCLOPROPYL KETONE AND A METHOD FOR THE PREPARATION THEREOF

[75] Inventors: Marco P. Burello, Cleveland; Jeffrey G. Stack, Painesville, both of Ohio; David A. Cortes, Fairless Hills, Pa.

[73] Assignee: American Cyanamid Company, Wayne, N.J.

[21] Appl. No.: 161,382

[22] Filed: Dec. 2, 1993

Related U.S. Application Data

[63] Continuation of Ser. No. 909,258, Jul. 6, 1992, abandoned.

[51] Int. Cl.$^5$ ............................................. C07C 209/36
[52] U.S. Cl. ..................................... 564/416; 568/306
[58] Field of Search ......................... 564/416; 568/306

[56] References Cited

U.S. PATENT DOCUMENTS

| | | | |
|---|---|---|---|
| 3,268,533 | 8/1966 | Freed et al. | 260/268 |
| 4,075,346 | 2/1978 | Sasajima et al. | 424/267 |
| 5,107,023 | 4/1992 | Brady et al. | 564/305 |

FOREIGN PATENT DOCUMENTS

WO92/00952  1/1992  European Pat. Off. .
2244473  4/1975  France .

OTHER PUBLICATIONS

Chemical Art & Pharmaceutical Bulletin vol. 9, (1961), pp. 719–721.
Yakugaku Zasshi, vol. 88 (8), pp. 1050–1053 (1968).
Organic Syntheses, Coll. vol. IV, pp. 597–600 (1958).
Cannon et al., "Methyl Cyclopropyl Ketone"; Organic Syntheses, Collective vol. 4, Wiley & Sons (1958).
CA54:15306; Bennett et al., 10 Aug. 1960.
CA105:93715m, Shive et al., Sep. 1986.

*Primary Examiner*—Glennon H. Hollrah
*Attorney, Agent, or Firm*—Peggy A. Climenson

[57] ABSTRACT

There is provided o-nitrophenyl cyclopropyl ketone, a key intermediate in the manufacture of the crop-selective, herbicidal agent 1-{[o-(cyclopropylcarbonyl)-phenyl]sulfamoyl}-3-(4,6-dimethoxy-2-pyrimidinyl)urea and a method for the preparation of said ketone from dihydro-3-acetyl-2(3H)-furanone and o-nitrobenzoyl halide.

11 Claims, No Drawings

HERBICIDE INTERMEDIATE O-NITROPHENYL CYCLOPROPYL KETONE AND A METHOD FOR THE PREPARATION THEREOF

This is a continuation of application Ser. No. 07/909,258 filed on Jul. 6, 1992.

BACKGROUND OF THE INVENTION

The crop-selective, herbicidal agent 1-{[9-(cyclopropylcarbonyl)phenyl]sulfamoyl}-3-(4,6-dimethoxy-2-pyrimidinyl)urea is described in U.S. Pat. No. 5,009,699. This unique sulfamoyl urea derivative demonstrates a superior margin of safety toward crop plants, especially rice plants, while concomitantly controlling troublesome broadleaf weeds and sedges.

The compound, 4-halo-2,-nitrobutyrophenone, and its preparation via the reaction of dihydro-3-(o-nitrobenzoyl)-2(3H)-furanone and hydrogen halide is described in U.S. Pat. No. 4,075,346. This patent describes the use of 4-halo-butyrophenone in the preparation of 4-(secondaryamino)-butyrophenone derivatives and their use as central nervous system depressants. It has now been found that 4-halo-2'-nitrobutyrophenone may be employed as a precursor to o-nitrophenylcyclopropyl ketone, a key intermediate in the manufacture of the crop-selective, herbicidal agent 1-{[(o-(cyclopropylcarbonyl)phenyl]sulfamoyl}-3-(4,6-dimethoxy-2-pyrimidinyl)urea.

It is an object of this invention to provide a key intermediate in the manufacture of this important crop-selective herbicidal agent.

It is another object of this invention to provide an efficient and integrated method for the preparation of this key intermediate.

It is a further object of this invention to provide a method of preparation for o-aminophenyl cyclopropyl ketone, also an important intermediate compound in the preparation of 1-{[o-(cyclopropyl-carbonyl)phenyl]sulfonyl}-3-(4,6-dimethoxy-2-pyrimidinyl)urea.

SUMMARY OF THE INVENTION

The present invention relates to o-nitrophenyl cyclopropyl ketone, a key intermediate in the manufacture of the crop-selective herbicidal agent 1-{[o-(cyclopropylcarbonyl)phenyl]sulfamoyl}-3-(4,6-dimethoxy-2-pyrimidinyl)urea, a method for the preparation thereof and a method for the preparation of o-aminophenyl cyclopropyl ketone. It has now been found that o-nitrophenyl cyclopropyl ketone may be prepared in an efficient and integrated method from the readily available starting materials, dihydro-3-acetyl-2(3H)-furanone and o-nitrobenzoyl halide.

DETAILED DESCRIPTION OF THE INVENTION

The invention herein described provides o-nitrophenyl cyclopropyl ketone, a process for the preparation thereof and a process for the preparation of o-aminophenyl cyclopropyl ketone. A description of o-aminophenyl cyclopropyl ketone and its use in the manufacture of an important crop-selective herbicidal agent is found in U.S. Pat.

Advantageously, this key intermediate, o-nitrophenyl cyclopropyl ketone, may be prepared in an efficient and integrated process from readily available starting materials. In accordance with the method of invention dihydro-3-acetyl-a(3H)-furanone is reacted with about 0.5–1.0 molar equivalents of magnesium $C_1$–$C_4$alkoxide at about 0°–25° C. to form an intermediate, the intermediate is reacted with at least one molar equivalent of o-nitrobenzoyl halide in the presence of a solvent at about 15°–35° C. to form a second intermediate, the second intermediate is heated in the presence of water to form dihydro-3-(o-nitrobenzoyl)-2-(3H)-furanone, the furanone is reacted with a hydrogen halide to form 4-halo-2'-nitrobutyrophenone and the butyrophenone is cyclized in the presence of a base to give o-nitrophenyl cyclopropyl ketone. The reaction sequence using o-nitrobenzoyl chloride as the o-nitrobenzoyl halide starting material is illustrated in Flow Diagram I wherein X designates halogen.

FLOW DIAGRAM I

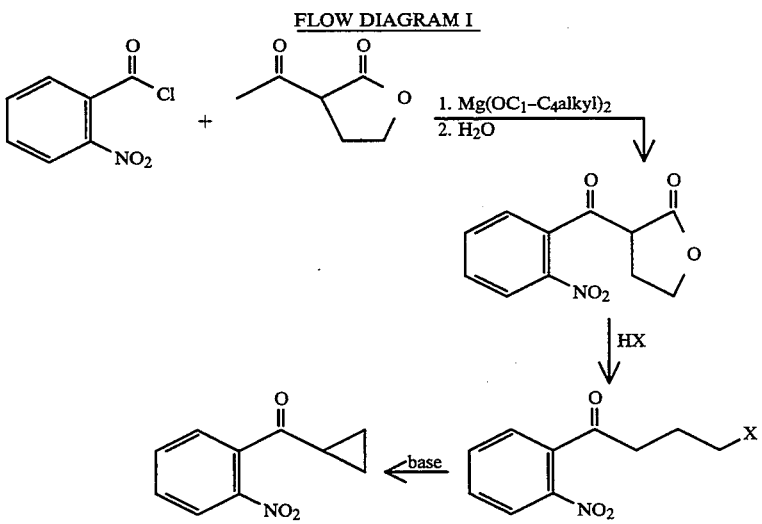

Beneficially, the o-nitrophenyl cyclopropyl ketone may be reduced in the presence of hydrogen and a catalyst to give o-aminophenyl cyclopropyl ketone. The reaction is shown in Flow Diagram II.

FLOW DIAGRAM II

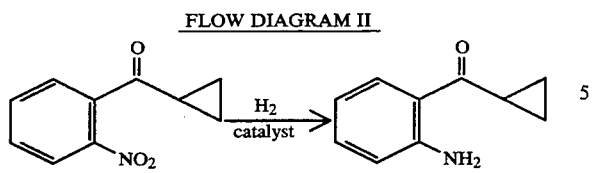

Solvents suitable for use in the method of the invention are those solvents which are immiscible in water such as aromatic hydrocarbons, dialkyl ethers, halogenated alkanes and the like, preferably aromatic hydrocarbons. When such solvents are used, for example toluene, xylene, etc., the reaction steps may be integrated such that the reaction products may be carried on to the subsequent steps as a solution in the organic phase without time-consuming and potentially wasteful isolation procedures. Among the magnesium alkoxides which may be used in the inventive method are magnesium $C_1$–$C_4$ alkoxides preferably those which are readily available such as magnesium methoxide or magnesium ethoxide. Similarly, the o-nitrobenzoyl halides and hydrogen halides which may be employed in the inventive method include those most commonly available such as chlorides or bromides.

Among the bases suitable for use in the cyclization step of the inventive method are those having a pKa greater than, or equal to, 10, such as organic amines, alkali metal carbonates or alkali metal hydroxides, preferably alkali metal hydroxides such as sodium hydroxide and potassium hydroxide. Hydrogenation catalysts include those well-known in the art such as platinum on carbon or palladium on carbon.

The rate of the decarboxylation/halogenation step is directly related to the concentration of the reagents, i.e. the more concentrated the organic solvent solution of dihydro-3-(o-nitrobenzoyl)-2(3H)-furanone and the more concentrated the hydrogen halide solution, the faster the reaction rate. Therefore, increased concentration of reactants yields increased reaction rate and productivity.

It is a feature of this invention that the individual preparative steps may be integrated by the use of a single, suitable, water-immiscible solvent such as toluene. The advantages of this feature include the elimination of costly, potentially wasteful and time-consuming isolation procedures.

The invention is further illustrated in the Examples set forth below and is not to be deemed limited thereby, except as defined in the claims.

The terms TLC, HPLC and LC designate thin layer chromatography, high performance liquid chromatography and liquid chromatography, respectively. The terms [13]NMR and $^{13}$CNMR designate proton and carbon-13 nuclear magnetic resonance, respectively. All parts are parts by weight unless otherwise noted.

EXAMPLE 1

Preparation and isolation of dihydro-3-(o-nitrobenzoyl-2(3H)-furanone

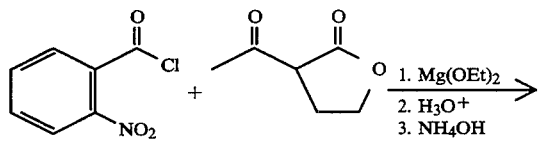

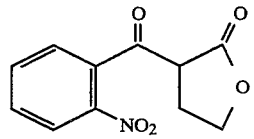

A mixture of Mg(OEt)$_2$ (30.9 g, 0.27 mole) in toluene is treated with dihydro-3-acetyl-2(3H)-furanone (77 g, 0.55 mole) at 5°–10° C., stirred for 1 hour at 25°–30° C., treated with a solution of o-nitrobenzoyl chloride (92.8 g, 0.50 mole) in toluene at 30°–35° C., stirred at 25°–35° C. for 1–2 hours, heated at 60° C. for 1 hour, cooled to 30° C., treated with water and 96% H$_2$SO$_4$ (15 g) and stirred for 0.5 hour. The phases are separated and the aqueous phase is extracted with ethyl acetate. The organic phases are combined, treated with aqueous NH$_4$OH, stirred for 5–10 minutes and separated. The organic phase is further extracted with aqueous NH$_4$OH. The aqueous phases are combined and acidified to pH 5.5 with 96% H$_2$SO$_4$ at 14°–20° C. The resultant precipitate is removed by filtration to give the title product as a white solid, 91.3 g, (77.7% yield), 85–90% pure by NMR analysis, identified by $^1$H and $^{13}$CNMR.

EXAMPLE 2

Preparation and isolation of 4-chloro-2'-nitrobutyrophenone

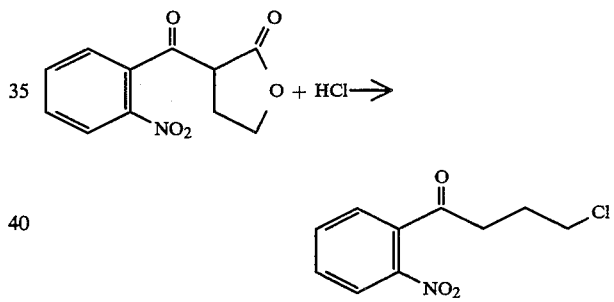

A mixture of dihydro-3-(o-nitrobenzoyl-2(3H)-furanone (2.0 g, 8.5 mmole) in 10 g of 37% HCl solution is stirred at 70° C. until reaction is complete by TLC, cooled to room temperature and extracted with toluene. The organic extracts are combined and concentrated in vacuo to give the title product as a golden oil, 1.84 g (95% yield), 99% pure by HPLC analysis, identified by $^1$HNMR.

Using essentially the same procedure and employing 48% HBr, 4-bromo-2'-nitrobutyrophenone is obtained as a brown solid, identified by $^1$HNMR and HPLC analysis.

EXAMPLE 3

Preparation and isolation of o-nitrophenyl cyclopropyl ketone

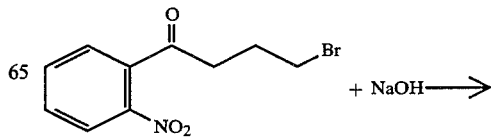

-continued

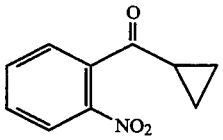

A stirred mixture of 4-bromo-2'-nitrobutyrophenone (3.44 g, 0.013 mole) and NaOH (0.76 g, 0.019 mole) in water is heated at reflux temperature until reaction is complete by TLC, cooled to room temperature and extracted with diethyl ether. The ether extracts are combined, dried over Na₂SO₄ and concentrated in vacuo to give a dark brown liquid residue. The residue is taken up in diethyl ether, filtered through silica gel and concentrated in vacuo to give the title product as a yellow oil, identified by ¹HNMR.

Using essentially the same procedure but employing 4-chloro-2'-nitrobutyrophenone as the starting material, the title product is obtained as a yellow oil in 98% yield and 99% purity by HPLC analysis, identified by ¹HNMR.

EXAMPLE 4

Preparation of o-aminophenyl cyclopropyl ketone

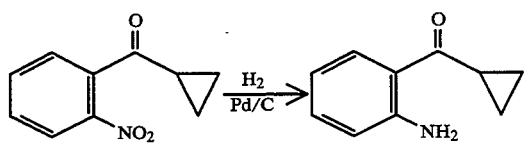

A mixture of o-nitrophenyl cyclopropyl ketone (100 mg, 0.52 mmole) and a catalytic amount of 10% Pd on carbon in methanol is stirred under hydrogen at atmospheric pressure until reaction is complete by TLC. The reaction mixture is filtered and the filtrate is concentrated in vacuo to give a bright yellow oil. The oil is flash chromatographed to give the title product as an off-white crystalline solid, 72 mg (85% yield), identified by ¹HNMR.

EXAMPLE 5

Preparation of dihydro-3-(o-nitrobenzoyl)-2(3H)-furanone (Integrated Step 1)

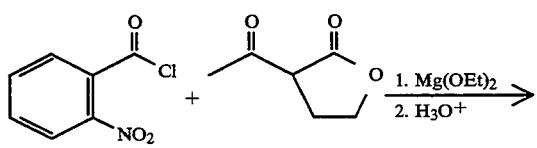

A mixture of Mg(OEt)₂ (63 g, 0.55 mole) in toluene, under N₂, is treated with dihydro-3-acetyl-(3H)-furanone (141 g, 1.10 mole) at 7°-10° C. over a 15 minute period and stirred at 25°-30° C. for 2 hours. The resultant reaction mixture is treated with a solution of o-nitrobenzoyl chloride (185.7 g, 1.0 mole) in toluene at 25°-35° C. over a 45 minute period, stirred at ambient temperatures for 1.75 hours, treated with 400 mL H₂O and heated at 60°-75° until reaction is complete by LC analysis. The resultant reaction mixture is cooled to room temperature and the phases are separated to give the title product as a toluene solution, 875 g, 18% desired product by LC analysis (67% yield). The product solution is used as is in Example 6.

EXAMPLE 6

Preparation of 4-chloro-2'-nitrobutyrophenone (Integrated step 2)

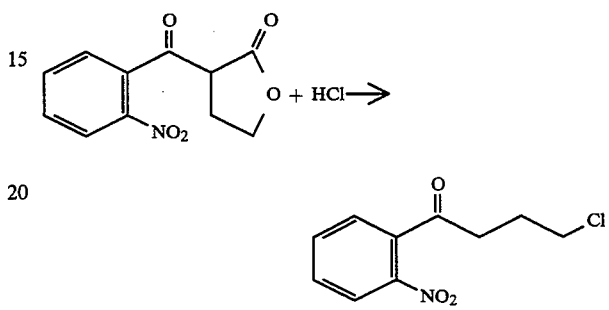

The 18% solution of dihydro-3-(o-nitrobenzoyl)-2(3H)furanone in toluene obtained in Example 5 (450 g, 0.34 mole furanone) is treated, with stirring, with 37% HCl (48 g, 0.60 mole HCl), heated at reflux temperature for 6-11 hours, until reaction is complete by LC analysis, cooled to 35°-45° C. and allowed to settle. The phases are separated to give the title product as a toluene solution, 425 g. The product solution is used as is in Example 7.

EXAMPLE 7

Preparation of o-nitrophenyl cyclopropyl ketone (Integrated step 3)

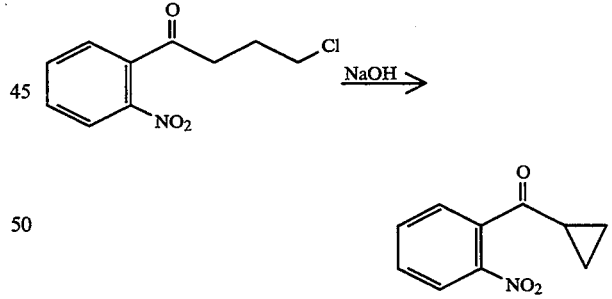

The 13.8% toluene solution of 4-chloro-2'-nitrobutyrophenone obtained in Example 6 is treated, with stirring, first with 90 mL water and second with 50% NaOH (48 g, 0.6 mole NaOH). The resultant reaction mixture is allowed to exotherm, then is heated at 85°-90° C. for 2-3 hours, cooled to room temperature and allowed to settle. The phases are separated and the organic phase is washed with water. The aqueous phases are combined and washed with toluene. The organic phases are combined and concentrated in vacuo to give the title product as a toluene solution, 235 g, 23.6% title product by LC analysis (91% yield from furanone). The product solution is used as is in Example 8.

EXAMPLE 8

Preparation of o-aminophenyl cyclopropyl ketone
(Integrated step 4)

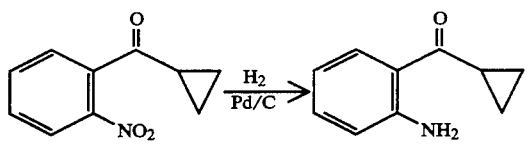

A mixture of the 23.6% toluene solution of o-nitrophenyl cyclopropyl ketone obtained in Example 7 (232.3 g, 0.286 mole ketone) and 2.86 g of 5% Pd/C catalyst is placed under $H_2$ at 32–56 psig in a Parr hydrogenator. The hydrogen uptake is monitored and when the reaction is complete, the reaction mixture is filtered and concentrated in vacuo to give the title product, 39.5 g, 86.3% pure by HPLC analysis (73.9% yield).

What is claimed is:

1. A method for the intergrated preparation of o-nitrophenyl cyclopropyl ketone which consists essentially of reacting dihydro-3-acetyl-2(3H)-furanone with about 0.50–1.0 molar equivalents of magnesium $C_1$-$C_4$alkoxide at about 0°–25° C. to form an intermediate, reacting said intermediate with at least one molar equivalent of o-nitrobenzoyl halide in the presence of a solvent at about 15°–35° C. to form a second intermediate, heating the second intermediate in the presence of water to form dihydro-3-(o-nitrobenzoyl)-2(3H)-furanone, reacting the furanone with a hydrogen halide to form 4-halo-2'-nitrobutyrophenone and cyclizing the butyrophenone in the presence of a base to give o-nitrophenyl cyclopropyl ketone.

2. The method according to claim 1 wherein the solvent is an aromatic hydrocarbon.

3. The method according to claim 2 wherein the solvent is toluene.

4. The method according to claim 1 wherein the magnesium $C_1$-$C_4$alkoxide is magnesium methoxide or magnesium ethoxide.

5. The method according to claim 1 wherein the hydrogen halide is hydrogen chloride or hydrogen bromide.

6. The method according to claim 1 wherein the base is an alkali metal hydroxide.

7. The method according to claim 6 wherein the alkali metal hydroxide is sodium hydroxide or potassium hydroxide.

8. A method for the intergrated preparation of o-aminophenyl cyclopropyl ketone which consists essentially of reacting dihydro-3-acetyl-2(3H)-furanone with about 0.50–1.0 molar equivalents of magnesium $C_1$-$C_4$alkoxide at about 0°–25° C. to form an intermediate, reacting said intermediate with at least one molar equivalent of o-nitrobenzoyl halide in the presence of a solvent at about 15°–35° C. to form a second intermediate, heating the second intermediate in the presence of water to form dihydro-3-(o-nitrobenzoyl)-2(3H)-furanone, reacting the furanone with a hydrogen halide to form 4-halo-2'-nitrobutyrophenone, cyclizing the butyrophenone in the presence of a base to give o-nitrophenyl cyclopropyl ketone and hydrogenating the nitrophenyl ketone in the presence of a catalyst to give o-aminophenyl cyclopropyl ketone.

9. The method according to claim 8 wherein the solvent is an aromatic hydrocarbon.

10. The method according to claim 9 wherein the solvent is toluene.

11. The method according to claim 8 wherein the base is an alkali metal hydroxide.

* * * * *